United States Patent [19]

Pearce, III

[11] Patent Number: 4,536,388

[45] Date of Patent: Aug. 20, 1985

[54] PEST CONTROL DEVICE COMPRISING α-CYANO-3-PHENOXYBENZYL 2-(2-CHLORO-4-TRIFLUOROME-THYLANILINO)-3-METHYLBUTANOATE

[75] Inventor: Robert C. Pearce, III, Arlington, Tex.

[73] Assignee: Zoecon Corporation, Palo Alto, Calif.

[21] Appl. No.: 514,738

[22] Filed: Jul. 18, 1983

[51] Int. Cl.$^3$ .................. A61K 13/00; A01N 37/34; A01N 37/00; A01N 43/36
[52] U.S. Cl. .................................. 424/28; 424/16; 424/19; 424/78; 514/521; 514/769; 514/785
[58] Field of Search ................ 424/304, 305, 16, 19, 424/28, 78, 78, 274

[56] References Cited

U.S. PATENT DOCUMENTS

| | | | |
|---|---|---|---|
| 3,852,416 | 12/1974 | Grubb et al. | 424/16 |
| 3,944,662 | 3/1976 | Miller, Jr. et al. | 424/19 |
| 4,195,075 | 3/1980 | Miller | 424/16 |
| 4,243,819 | 1/1981 | Henrick | 424/274 |
| 4,265,876 | 5/1981 | Feakin | 424/28 |

Primary Examiner—Nicky Chan
Assistant Examiner—C. Joseph Faraci
Attorney, Agent, or Firm—Hana Dolezalova; Jacqueline S. Larson

[57] ABSTRACT

A pest control device, such as an ear tag, for controlling pests such as flies, fleas and ticks on animals such as cattle and other livestock or pet animals which comprises a polymeric resin matrix and the pesticidally active compound α-cyano-3-phenoxybenzyl 2-(2-chloro-4-trifluoromethylanilino)-3-methylbutanoate.

11 Claims, No Drawings

PEST CONTROL DEVICE COMPRISING α-CYANO-3-PHENOXYBENZYL 2-(2-CHLORO-4-TRIFLUOROMETHYLANILINO)-3-METHYLBUTANOATE

This invention relates to a method and a device for the effective and long-term control of harmful pests such as flies, fleas and ticks on cattle and other livestock or pet animals. More particularly, it relates to a pest control device, in the form of, for example, an ear tag, which comprises a polymeric resin matrix and the pesticidally active compound α-cyano-3-phenoxybenzyl 2-(2-chloro-4-trifluoromethylanilino)-3-methylbutanoate.

Livestock can be greatly troubled by pests such as hornflies, face flies, Gulf Coast ticks, spinose ear ticks, etc., which can cause not only irritation to the animal and interference with its normal feeding and grazing habits but also oftentimes infection and illness.

A recently developed method for controlling pests on livestock is based on slow release pesticidal generators, which can be prepared by mixing a particular pesticide with a resinous substance which releases the pesticide over an extended period of time. Such pesticidal generators are described, for example, in U.S. Pat. Nos. 3,318,769, 3,852,416 and 3,944,662. In particular, pest control devices attachable to the ears of livestock utilizing slow-release pesticide technology are disclosed in U.S. Pat. Nos. 3,765,200 and 3,942,480, which describe use of 2,2-dichlorovinyl dimethyl phosphate (DDVP) for repelling ticks; U.S. Pat. No. 4,195,075, describing α-cyano-3-phenoxybenzyl α-isopropyl-4-chlorophenylacetate (fenvalerate) for the control of flies and ticks; and U.S. Pat. No. 4,265,876, describing 3-phenoxybenzyl 2,2-dimethyl-3-(2,2-dichlorovinyl)cyclopropanecarboxylate (permethrin) and α-cyano-3-phenoxybenzyl 2,2-dimethyl-3-(2,2-dichlorovinyl)cyclopropanecarboxylate for controlling flies and ticks.

The pesticide which is utilized in the method and device of the present invention is α-cyano-3-phenoxybenzyl 2-(2-chloro-4-trifluoromethylanilino)-3-methylbutanoate, also known by the common name "fluvalinate," which can exist in a number of stereoisomeric forms. Accordingly, the invention includes a single stereoisomer or a combination of two or more stereoisomers of the pesticidally-active compound. A preferred embodiment of the present invention utilizes (R,S)-α-cyano-3-phenoxybenzyl(R)-2-(2-chloro-4-trifluoromethylanilino)-3-methylbutanoate. Fluvalinate and its preparation are disclosed in U.S. Pat. No. 4,243,819. The preferred diastereomeric pair and its preparation are disclosed in U.S. Pat. No. 4,260,633.

The active ingredient α-cyano-3-phenoxybenzyl 2-(2-chloro-4-trifluoromethylanilino)-3-methylbutanoate is present in the pest control device in a pesticidally effective amount, generally from about 1% to about 20% by weight of the total composition. Concentrations of about 2% to about 10% by weight are preferred.

The pest control device of the present invention comprises the aforesaid pesticide dispersed in a polymeric resin matrix. The polymeric resin matrix is comprised of a polymeric resin and, optionally, a suitable plasticizer.

In general, any thermoplastic or thermosetting resin, including elastomers, compatible with the pesticide is suitable as the polymeric resin. The resin needs to have adequate strength and sufficient durability to withstand normal wear. Further, the resin must be one which will permit adequate release of the pesticide. Examples of suitable substances are polyolefins (for example, polyethylene and polypropylene); polyacrylates (for example, polymers and copolymers of methyl acrylate, ethyl acrylate and methyl methacrylate); polymers of vinyl compounds (for example, polystyrene); polyvinyl halides (for example, polyvinyl chloride); polyvinyl acetals (for example, polyvinyl butyral); polyvinylidene compounds (for example, polyvinylidene chloride); synthetic and natural elastomers (for example, *hevea brasiliensis*, cis-1,4-polyisoprene, polybutadiene and SBR rubber); urea-formaldehyde and melamine-formaldehyde resins; epoxy resins (for example, polymers of polyglycidyl ethers of polyhydric phenols); cellulose plastics (for example, cellulose acetate and cellulose butyrate); and polyurethanes. Generally, the polymeric resin comprises from about 35% to about 75% by weight of the total composition, with amounts of from about 40% to about 70% by weight being preferred.

Because one embodiment of the pesticide control device of the present invention is an ear tag for attachment to cattle and other livestock, the polymer resin material should be sufficiently strong yet flexible for this purpose. Thus, optionally plasticized thermoplastic resins are preferred as the polymer resin matrix. Suitable thermoplastic resins are polyvinyl resins such as polyvinyl halides (including polyvinyl chloride, PVC), polyvinyl esters, polyvinylidine chloride and chlorinated polyethylene. Plasticizers which may be employed to plasticize the thermoplastic resins include esters of polybasic acids such as phthalate esters (for example, dioctyl phthalate, diphenyl phthalate and dicyclohexyl phthalate), sebacate esters (for example, dipentyl sebacate, n-butylbenzyl sebacate and dibenzyl sebacate), adipate esters (for example, dioctyl adipate, dicapryl adipate and di-isobutyl adipate) and citrate esters. The particular plasticizer employed will depend upon its compatibility with the pesticide and with the particular resin used. The plasticizer must be one which will not exude from the particular resin at normal temperatures and conditions. In general, the plasticizer comprises from 0% to about 45% by weight of the total composition, with amounts of from about 25% to about 40% being preferred.

When the device of the present invention is in the form of an ear tag, polyvinyl chloride plasticized with dioctyl adipate, dioctyl phthalate or butyl benzyl phthalate is the preferred polymeric resin matrix.

Other ingredients such as stabilizers, impact modifiers, dyes, fillers, anti-oxidants, secondary plasticizers, insect attractants and other pesticides can be incorporated into the pest control device of the present invention, usually in amounts of 1% or less to about 15% by weight of the total composition. See Sears & Darby, *The Technology of Plasticizers* (John Wiley & Sons, 1982) for a description of said other ingredients and plasticizers.

The pest control device of the present invention can be prepared by a variety of means depending on the polymeric resin matrix used. Suitable means of preparation include, for example, forming a dry blend of a thermoplastic resin, plasticizer and pesticide and using sufficient mixing and heat to obtain a homogeneous melt which can be cast, extruded or injection molded into a desired shape such as ear tags, bands, collars, bars, or the like. Another method of preparation is to disperse the pesticide into the ingredients of a thermo-setting composition, which composition is subsequently shaped and cured.

The present invention includes within its scope a method of controlling pests such as flies, fleas and ticks on or in the very near vicinity of cattle and other livestock or pet animals which comprises attaching to the animal a polymeric resin matrix containing a pesticidally effective amount of α-cyano-3-phenoxybenzyl 2-(2-chloro-4-trifluoromethylanilino)-3-methylbutanoate.

One embodiment of the device is an ear tag for attaching to the ear of the animal, which tag can take the form of a single element, one end of which is capable of piercing the ear, or of a two-piece tag, based on clamps, pins or studs. Representatives of suitable tags are described in U.S. Pat. Nos. 3,260,007, 3,388,492, 3,512,289, 3,595,201, 3,731,414 and 3,934,368.

Other embodiments of the invention include bands which may be wrapped around and secured to the base of the animal's ears or horns. The device of the present invention is especially effective against pests such as the face fly and horn fly and, hence, locating the device on or in close proximity to the face/head of the animal is advantageous. Attachment to the end of the animal's tail would likewise be advantageous since cattle and other livestock often swish their tails around the face and head to ward off flies and other pests.

The device of the present invention can be effectively employed as a collar, especially in the form of a strong, flexible polymer matrix such as PVC, polyurethane and the like. Alternatively, a device in the form of a bar or band can be affixed to the regular collar of the animal. Also, a device of the present invention in the form of a small strip may be secured to the regular ear tag of the animal such as by stapling, gluing or riveting the strip to the ear tag. See U.S. Pat. Nos. 3,811,413, 3,900,981, 3,949,708, 4,059,074, 4,184,452 and 4,366,777 for examples of collar and tag devices.

The following examples are provided to illustrate the practice of the present invention. Temperature is in degrees Fahrenheit. "RT" means room temperature. The term "% w" indicates percentage by weight of the total composition.

EXAMPLE 1

Polyvinyl chloride (PVC) powder (46.5% w, 1116.0 g) is mixed in a high intensity mixer (Henschel) until the polymer reaches 140°. To this is added, with mixing, 2.3% w (55.2 g) of epoxidized soybean oil, 27.7% w (664.8 g) of dioctyl phthalate, 2.3% w (55.2 g) of a PVC stabilizer and 21.0% w (504.0 g) of racemic α-cyano-3-phenoxybenzyl 2-(2-chloro-4-trifluoromethylanilino)-3-methylbutanoate. The blend is heated to 175°, with mixing, after which 0.2% w (4.8 g) of stearic acid is slowly added and the temperature is returned to 175°. After a homogeneous blend is obtained, it is then cooled to RT.

The blend is fed into an injection molding machine, where it is heated (front zone, 150° center zone, 250°; nozzle, 320°) and injection molded into dies to yield ear tags containing 20.0% w of α-cyano-3-phenoxybenzyl 2-(2-chloro-4-trifluoromethylanilino)-3-methylbutanoate.

The epoxidized soybean oil is 2-ethylhexyl epoxytallate, known as Drapex 4.4, Argus Chemical Company.

The stabilizer is barium-zinc-phosphite stabilizer, Mark 1603, Argus Chemical Company.

The polyvinyl chloride is chosen from Ethyl SM250 (Ethyl Corporation), Oxy 9400 (Occidental Chemical Corporation) and Tenneco 250-3 (Tenneco).

EXAMPLE 2

To 47.47% w (1087.1 g) of PVC is added, with mixing, 0.50% w (11.45 g) of phthalo blue and 2.0% w (45.8 g) of diarylide yellow. The blend is heated to 150° with mixing. A pre-mix of 8.73% w (199.9 g) of (R,S)-α-cyano-3-phenoxybenzyl (R)-2-(2-chloro-4-trifluoromethylanilino)-3-methylbutanoate (91.6% A.I.) and 5.0% w (114.5 g) of butyl benzyl phthalate is added to the blend as mixing is continued, followed by the addition of 4.0% w (91.6 g) of a PVC stabilizer (barium-zinc) and 32.0% w (732.8 g) of dioctyl phthalate. The resulting blend is heated to 185°, 0.3% w (45.8 g) of stearic acid is added, and the temperature is raised to 190°. The blend is then cooled to RT.

The blend is fed into an injection-molder, is heated (front zone, 340°; center zone, 340°; rear zone, 320°; nozzle, 75°) and is molded to yield ear tags containing 8% w of (R,S)-α-cyano-3-phenoxybenzyl (R)-(2-chloro-4-trifluoromethyl-anilino)-3-methylbutanoate.

Following the above procedure, the compositions a, b, c, d and e, given in Table I below, are prepared to yield ear tags containing, respectively, 10% w, 8% w, 6% w, 4% w and 2% w of (R,S)-α-cyano-3-phenoxybenzyl (R)-2-(2-chloro-4-trifluoromethylanilino)-3-methylbutanoate.

TABLE I

| Material | Composition | | | | |
|---|---|---|---|---|---|
| | a | b | c | d | e |
| polyvinyl chloride | 47.47[1] | 47.47 | 47.47 | 47.47 | 47.47 |
| phthalo blue | 0.50 | 0.50 | 0.50 | 0.50 | 0.50 |
| diarylide yellow | 2.00 | 2.00 | 2.00 | 2.00 | 2.00 |
| pesticide[2] | 10.92 | 8.73 | 6.55 | 4.50 | 2.25 |
| butyl benzyl phthalate | 5.00 | 5.00 | 5.00 | 5.00 | 5.00 |
| barium-zinc stabilizer | 4.00 | 4.00 | 4.00 | 4.00 | 4.00 |
| dioctyl phthalate | 29.81 | 32.00 | 34.18 | 36.23 | 38.48 |
| stearic acid | 0.30 | 0.30 | 0.30 | 0.30 | 0.30 |

[1] amounts given in % w.
[2] (R,S)-α-cyano-3-phenoxybenzyl (R)-2-(2-chloro-4-trifluoromethylanilino)-3-methylbutanoate (91.6% A.I.).

EXAMPLE 3

PVC (Ethyl SM250; 54.5% w, 4360 g) is mixed and heated to 150°. To this is added, with mixing, a pre-mix of 4.0% w (320 g) of a barium-zinc PVC stabilizer and 9.2% w (736 g) of (R,S)-α-cyano-3-phenoxybenzyl (R)-2-(2-chloro-4-trifluoromethylanilino)-3-methylbutanoate (89.3% A.I.), followed by the addition of 27.0% (2160 g) of dioctyl phthalate and 3.0% w (240 g) of butyl benzyl phthalate. The resulting blend is heated, with mixing, to 185°, after which 0.3% w (24 g) of stearic acis is added, the temperature is raised to 190° and 2.0% w (160 g) of orange dye (PMS 82734 TMB) is added. The blend is mixed for one minute and is the cooled to RT.

The blend is fed into an injection-molder, is heated (front zone, 340°; center zone, 340°; near zone, 320°; nozzle, 285°) and is molded to yield ear tags containing 8% w of (R,S)-α-cyano-3-phenoxybenzyl (R)-2-(2-chloro-4-trifluoromethylanilino)-3-methylbutanoate.

What is claimed is:

1. A pest control device for attachment to an animal which comprises a plasticized polyvinyl halide resin matrix having dispersed therein a pesticidally effective amount of the compound α-cyano-3-phenoxybenzl 2-(2- chloro-4-trifluoromethylanilino)-3-methylbutanoate wherein the polyvinyl halide resin matrix is present in the amount from about 35% to about 75% by weight of the total composition, the plasticizer is present in the amount of from about 25% to about 45% by weight of the total composition and the pesticide is present in the amount of from about 1% to about 20% by weight of the total composition.

2. A pest control device according to claim 1 wherein the plasticizer is dioctyl adipate, dioctyl phthalate or butyl benzyl phthalate.

3. A pest control device according to claim 2 wherein the polyvinyl halide resin is polyvinyl chloride.

4. A pest control device according to claim 3 wherein the pesticide is (R,S)-α-cyano-3-phenoxybenzyl (R)-2-(2-chloro-4-trifluoromethylanilino)-3-methylbutanoate.

5. A pest control device according to claim 1 in the form of a tag which is attachable to the ear of cattle and other livestock.

6. A pest control device according to claim 1 wherein the polyvinyl halide is present in the amount of from about 40% to about 70% by weight of the total composition, the plasticizer is present in the amount of from about 25% to about 40% by weight of the composition and the pesticide is present in the amount of from about 2% to about 10% by weight of the total composition.

7. A pest device according to claim 6 wherein the polyvinyl halide resin is polyvinyl chloride.

8. A pest control device according to claim 7 wherein the pesticide is (R,S)-α-cyano-3-phenoxybenzyl (R)-2-(2-chloro-4-trifluoromethylanilino)-3-methylbutanoate.

9. A method for controlling pests on animals which comprises attaching to said animal a pest control device of claim 1.

10. The method according to claim 9 wherein the polyvinyl halide resin matrix is in the form of an ear tag and is attached to the ear of cattle and other livestock.

11. The method according to claim 10 wherein the pesticide is (R,S)-α-cyano-3-phenoxybenzyl (R)-2-(2-chloro-4-trifluoromethylanilino)-3-methylbutanoate.

* * * * *